United States Patent [19]
Rantala

[11] Patent Number: 4,798,229
[45] Date of Patent: Jan. 17, 1989

[54] GAS FLOW CONSTRICTION MODULE

[75] Inventor: Börje Rantala, Helsinki, Finland

[73] Assignee: Instrumentarium Corp., Finland

[21] Appl. No.: 14,012

[22] Filed: Feb. 12, 1987

[30] Foreign Application Priority Data

Mar. 19, 1986 [FI] Finland ............... 861140

[51] Int. Cl.$^4$ .............................................. F15D 0/00
[52] U.S. Cl. ................................................... 138/42
[58] Field of Search ................. 138/40, 42, 44, 118.1, 138/178, 129, 132; 62/511, 504; 128/204.13, 207.15; 264/275, 278, 271.1, 279.1; 428/36

[56] References Cited

U.S. PATENT DOCUMENTS

| | | | |
|---|---|---|---|
| 2,393,854 | 1/1946 | Carpenter | 138/40 |
| 3,346,117 | 10/1967 | Page | 138/42 |
| 3,826,288 | 7/1974 | Cooper et al. | 138/118 |
| 4,276,333 | 6/1981 | Cobean | 428/371 |
| 4,605,059 | 8/1986 | Page | 165/163 |
| 4,619,317 | 10/1986 | Disselbeck | 165/163 |

Primary Examiner—Bernard Nozick
Attorney, Agent, or Firm—Andrus, Sceales, Starke & Sawall

[57] ABSTRACT

The invention relates to a gas flow constriction module for the distribution and control of the flow in a respiratory gas monitoring device. The constriction means is provided by a thin, long, plastic constriction tube (3) which is wound on a coil body (2), including couplings (5) in which said constriction tube (3) is cast. Also the part of constriction tube on the coil body can be cast in an adhesive. The arrangement serves to eliminate the problems that are otherwise involved in the use of a long, thin and slippery plastic tubing.

4 Claims, 1 Drawing Sheet

GAS FLOW CONSTRICTION MODULE

BACKGROUND OF THE INVENTION

The present invention relates to a gas flow constriction module, used in the gas handling system of a medical respiratory gas analyzer for the constriction, distribution and control of a flow.

In patient monitoring, the contents of respiratory gases are generally monitored by using a gas analyzer. In a so-called sidestream monitor, a sample of gas to be analyzed is passed from the respiratory tract of a patient or from respiratory tubes into a gas monitor for analysis. Since the gas often carries along some water, phlegm and dust, the sampling system must first of all be capable of separating some of these substances, which are highly detrimental to measuring sensors, and second of all, the device must be tolerant of these substances as possible without blocking.

Gas flow constriction is an essential part of both the sample flow control mechanism and the water separation system (see e.g. a water separation system disclosed in U.S. Pat. Nos. 4,382,806 and 4,304,578).

In addition to limiting the rate of gas flow, the flow constriction should exhibit several properties:
  constriction must not be of such a "small hole size" that it is blocked due to dust particles.
  The constriction must tolerate temporary filling with water, e.g. during washing, disinfection or water separator overload. Water must also be readily removable from the constriction.

These requirements are often fulfilled by using a long, thin plastic tube. However, such tube-formed constriction has several drawbacks, including mechanical vulnerability, difficult installation, connections to other tubes of different thicknesses are difficult, and 'slippery' plastics materials (e.g. teflon or polyethene) are not easily glued. A consequence of these drawbacks is poor productivity.

SUMMARY OF THE INVENTION

An object of the invention is to provide an improved gas flow constriction module which partially or completely eliminates the above-mentioned problems involved in the manufacture and use of a tube-formed constriction. This object is achieved in the invention on the basis of the characterizing features set out in the annexed claims.

DESCRIPTION OF THE DRAWINGS

One embodiment of the invention will now be illustrated with reference made to the accompanying drawings, in which.

DESCRIPTION OF THE ILLUSTRATED EMBODIMENT

Figure 1:
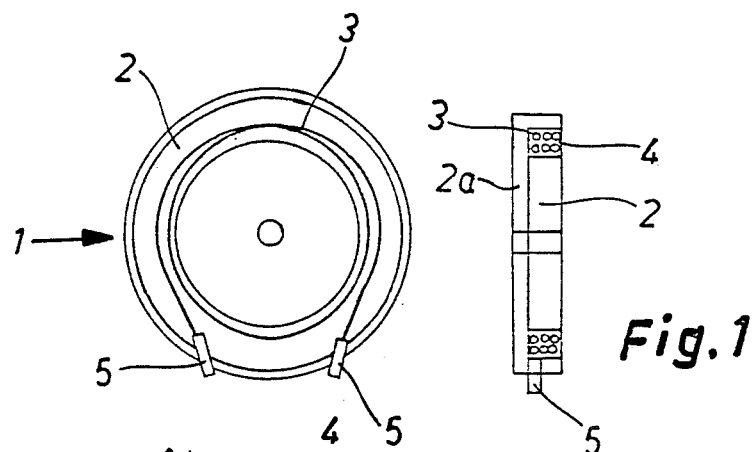
FIG. 1A is a plan view of the constriction module of the invention.
FIG. 1B is a transverse section of the constriction module.
Figure 2:
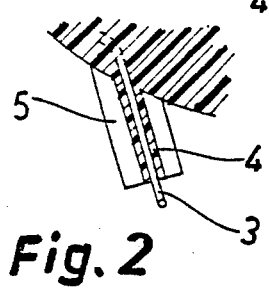
FIG. 2 is an enlarged fragmentary section showing the coupling construction.

FIGS. 1 and 1a illustrate a constriction module which comprises a molded plastic coil body 2 having a lid 2a and a constriction tube 3 is wound in body 2. Tube couplings 5 extend through the wall of the body 2 and receive the ends of the tube 3.

When a tube 3 has been wound in a coil body 2 and the ends of tube 3 pushed out of couplings 5, around said tube 3 is provided an epoxy resin casting or a similar casting, indicated by reference numeral 4, inside which said tube 3 remains at least within the extent of couplings 5 but preferably also within the extent of coil body 2.

Particularly the tube joints or couplings 5 provide a very essential part of the invention. Since, in joints 5 and partially or completely within the extent of coil body 2, said tube 3 is cast in epoxy resin 4, the constriction tube 3 itself need not be made of any gluable material; by virtue of casting, the tightness of a joint 5 does not require adhesion.

The end of constriction tube 3, extending beyond joint 5 after casting, is cut off.

Figure 3:
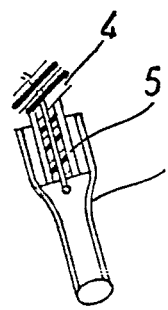
FIG. 3 is a view similar to FIG. 2 and showing the attachment of tubing to the coupling.

As illustrated in FIG. 3, a constriction module of the invention can be connected to other tubings of a monitoring device by means of a thick and flexible, e.g. silicone tubing 6 directly without the hazard of flexible tube 6 squeezing the constriction tube, causing increased flow resistance or eventually blocking the flow.

Figure 4:
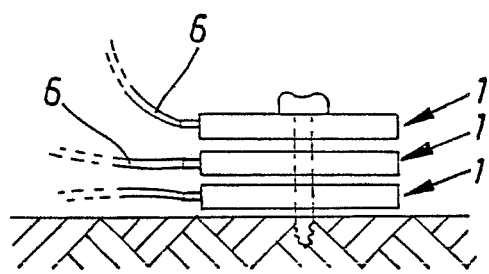
FIG. 4 is a schematic view illustrating the stacking of a plurality of constriction modules on a respiratory gas monitoring device.

The flat cylindrical shape of a restriction module makes it possible to lay a plurality of restriction modules mechanically on top of each other, as shown in FIG. 4. Thus, a cellular structure provides for easy installation inside a gas monitor.

Other advantages gained by the invention over an unsupported constriction tube structure, consisting of mere fitting tubes, include:
  a fragile constriction tube is well protected and not susceptible to deflection or damage
  a constriction tube can be entirely cast in epoxy resin or a similar adhesive for good mechanical stability. After all, the resistance to flow is proportional to the fourth power of a tube diameter and thus susceptible to deformation caused by mechanical and thermal stresses.

I claim:

1. A gas flow constriction module for the distribution and control of flow in a respiratory gas monitoring device, comprising a coil body having a bottom and a side wall defining an internal chamber, a pair of tubular couplings extending through said wall and communicating with said chamber, the outer ends of said couplings projecting outwardly of said wall, a thin long plastic coil constriction tube disposed within the chamber and supported on said bottom, the ends of the tube disposed within the respective couplings, and a rigid cast resin material bonding the projecting ends of the tube to the respective couplings, said couplings adapted to receive tubing to provide a connection between said tubing and said constriction tube.

2. The module of claim 1, wherein the portion of said tube disposed within said chamber is encased in said resin material.

3. The module of claim 1, and including a plurality of bodies disposed in stacked relation.

4. A gas flow constriction module for the distribution and control of a fluid in a respiratory monitoring device, comprising a body having a bottom and a side wall and defining and internal chamber, a thin plastic constriction tube disposed in coiled form within said chamber and supported by said bottom, said side wall having a pair of openings, a pair of rigid tubular connectors extending outwardly from said body and each having an internal passage communicating with the respective opening, the ends of the tube extending through the respective openings and disposed within the corresponding passages, and means for securing the ends of the tube within the passages of said couplings.

* * * * *